United States Patent [19]
Sheehy

[11] Patent Number: 5,660,796
[45] Date of Patent: Aug. 26, 1997

[54] SEPTUM PIERCER AND SAMPLE EXTRACTOR FOR PHYSIOLOGICAL SPECIMENS

[75] Inventor: Timothy M. Sheehy, Las Vegas, Nev.

[73] Assignee: Kloehn Instruments, Ltd., Las Vegas, Nev.

[21] Appl. No.: 743,521

[22] Filed: Sep. 19, 1991

[51] Int. Cl.$^6$ ............................................. B01L 3/02
[52] U.S. Cl. ........................... 422/100; 604/44; 604/45
[58] Field of Search ........................ 422/100; 73/864.22, 73/864.12, 863.85, 863.86, 863.87; 604/44–45

[56] References Cited

U.S. PATENT DOCUMENTS 5,078,970   1/1992   Teodorescu et al. ................. 422/100

FOREIGN PATENT DOCUMENTS 0496458   10/1950   Belgium .................. 604/44

*Primary Examiner*—Lyle A. Alexander
*Attorney, Agent, or Firm*—Donald D. Mon

[57] ABSTRACT

A septum piercer and sample extractor for removing a sample from a specimen contained in a container closed by a penetrable septum, a needle having a body with a sharp closed point on its first end. The needle extends axially and contains a first channel and a second channel, which extend toward the second end of the needle. A first side port passes through the body into the first channel. A second port passes through the body into the second channel. The first side port is axially farther from the second end than the second side port. The channels are both open near the second end of the needle. The needle is movable axially to pierce the septum. Its first end can be moved through the septum and into the container so that one of the ports is submerged in a fluid sample in the container while the other of the ports remains out of the sample. When one of the ports is submerged in the sample, gas can be forced through the channel leading to the other of the ports to force fluid from the sample through said submerged port.

4 Claims, 1 Drawing Sheet

SEPTUM PIERCER AND SAMPLE EXTRACTOR FOR PHYSIOLOGICAL SPECIMENS

SPECIFICATION

FIELD OF THE INVENTION

This invention relates to the safer removal of physiological samples from closed containers.

BACKGROUND OF THE INVENTION

Physiological specimens of fluids such as blood are collected in closed receptacles from which samples must later be removed for testing. One well-known type of container exemplifies the problem solved by this instant invention. This is the "Vacutainer", which is a glass vial closed by a stopper-like septum. It is sold evacuated so that when it is opened to a needle inserted into a vein or artery the vacuum inside the container draws blood into the container.

This closed container with its contents is centrifuged to settle the red cells and separate the plasma or serum as a supernatant liquid atop the red cells. The problem is how safely to extract some of the fluid for further use, when the fluid may contain material which is dangerous to the technician.

For many years, the removal of fluid from a specimen container was considered to be no more complicated than the removal of the stopper and the transfer of the fluid with a pipette. However, with the increasing dangers of some diseases carried in the blood such as AIDS and hepatitis, health workers who must work with blood. their employers, and society in general, have been justifiably concerned about physical contact with the blood samples. A preponderance of specimens are taken from persons who have or may have serious ailments. The operator does not know what risks may be in the sample. Often enough neither does the patient or the physician who ordered the test. Accordingly, every sample must be treated as though it is the worst possible example.

As a consequence there exists a conflict between necessary speed in order to keep tests affordable, and risks inherent in rapid handling. What is needed is a means quickly and safely to remove a sample from a container without exposing the operator to risks of contact with the fluid, or with a spray of the fluid.

Also, it is axiomatic that one sample must not be permitted to contaminate other samples. In some systems the same needle is used from sample to sample, requiring a cleansing and sterilizing step between each use of the needle. This requires additional expense by way of extra equipment or of added time, both of which increase the cost of the test.

Of course these objections have long been recognized, and efforts have been made to overcome them. Still there remain serious disadvantages and risks. Some of these would have been of little concern before the appearance of AIDS, but now they are. One example is the tendency of a spray, however slight, that can be generated when the septum is removed to give access to the contents of the container. This is not an insignificant risk, especially in a laboratory where many of these are removed per hour.

There are obvious means by which one can seek to alleviate this situation. Performing the manipulations in a hood or other negative air flow region is one of them Again, the cost of the installation and of the manipulations increases. Also there is the costs of simply removing the cap to carry out the procedure.

It is an object of this invention to provide a septum piercer and extractor which can obtain uncontaminated samples from containers affordably and without cross-contamination, and without any exposure of the operator to the specimen or sample.

BRIEF DESCRIPTION OF THE INVENTION

This invention is carried out with a rigid impermeable specimen container such as a glass vial having an open neck. The neck opens into a cavity which receives the specimen, usually but not always a quantity of blood.

A septum in the nature of a stopper closes the neck. The cavity is initially evacuated, and the septum is equipped with a needle to pierce a vein or an artery. The blood is brought into the cavity because of the reduced pressure in it. Known means keeps the device closed and sealed against leakage until it is used.

Whatever the arrangement, and this invention is not limited to use with evacuated containers, the laboratory receives the container closed and with the specimen inside.

According to this invention, a septum piercer and evacuator is provided as a two-channel needle with a sharpened tip. The channels are closed at the tip end (sometimes called by the "first end"), and each has a respective side port, one farther from the first end than the other.

To remove the test material, the needle is pressed through the septum until one side port is below the surface. Then air is pumped into the channel that leads to the other side port (this other side port preferably remains above the surface). Sample fluid then enters submerged side port and flows through it respective channel to a distribution point. The needle can be pressed move to follow the lowering surface if desired.

When enough sample has been withdrawn, the entire combination-needle, container and septum can be discarded. The septum was never removed, and there has been no contact with the specimen.

If desired, a momentary vacuum may be pulled on the channel with the air to tend to draw back into the container fluid which may remain in the needle. Instead, the needle may be withdrawn so both ports are above the fluid, and a brief very small burst of air may be injected which will blow the outflow channel clean, the effluent going to the receptacle that received the remainder of the sampler. These are optional techniques.

This invention will be fully understood from the following detailed description and the accompanying drawings, in which:

DETAILED DESCRIPTION OF THE INVENTION

Figure 1:
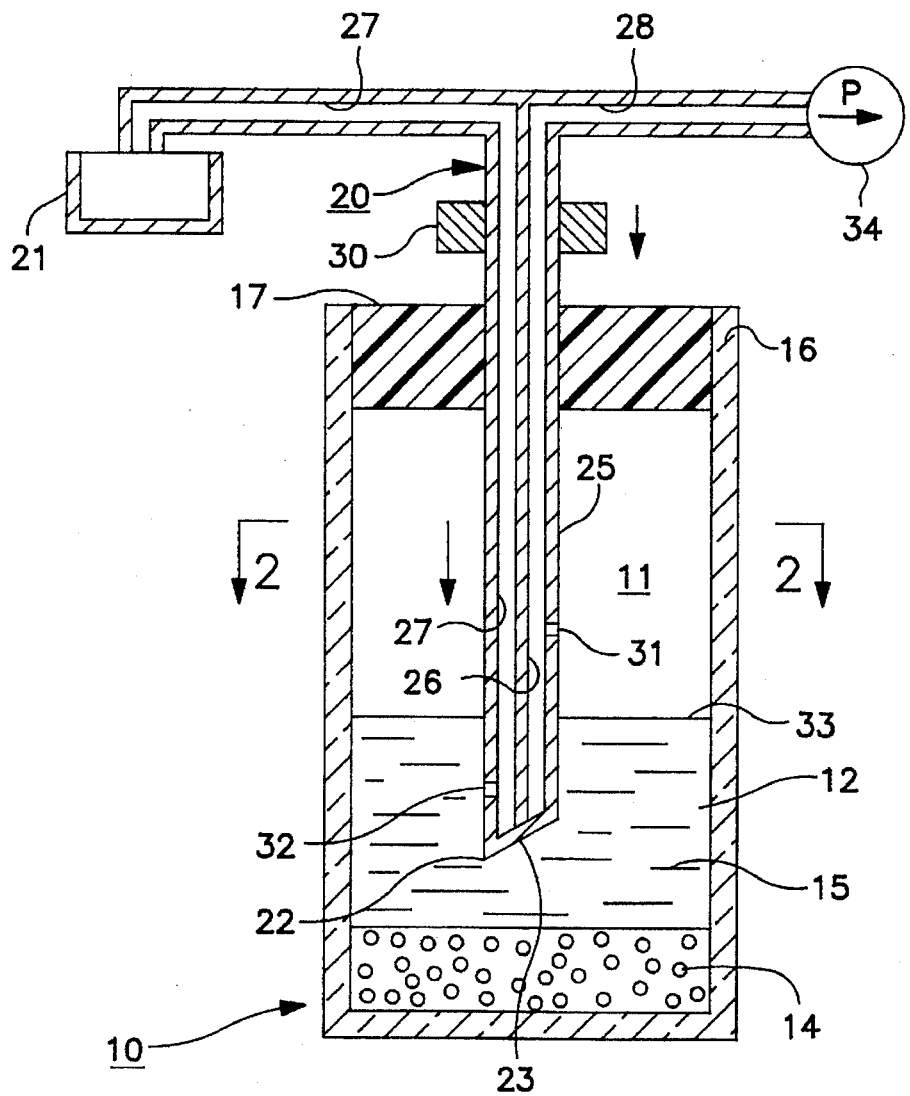
FIG. 1 is an axial cross-section partly in schematic notation, showing the presently preferred embodiment of the invention.
Figure 2:
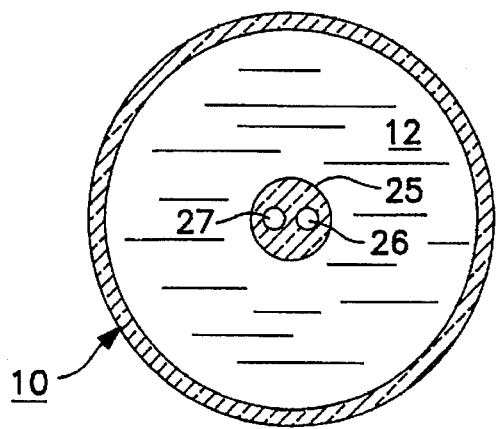
FIG. 2 is a cross-section taken at line 2—2 in FIG. 1.

FIG. 1 shows a specimen container 10 having a cavity 11 which has received a specimen 12 to be analyzed. This container may be, for example, a well-known Vacutainer, shown containing a blood specimen. The container has been centrifuged to separate the blood into its heavier red cells 14 and supernatant plasma or serum 15 above it. The function of this invention is to remove some of the plasma or serum without exposing the technician to contact with the blood, or with spray from the blood.

The container has a neck 16. In the illustration, the neck is a continuation of the cylindrical wall of what actually is a conventional vial. It is closed by a septum 17 in the nature of a stopper. The stopper is made of penetrable material, usually some kind of rubber or rubber-like substance. The container is sold closed and evacuated, and without the needle 20 shown piercing it. This needle is the subject of this invention.

Whatever the arrangement, the technician is confronted with the task of extracting some of the supernatant fluid and placing it elsewhere, perhaps in a separate container 21 or on a slide. The ultimate destination is of no concern to this invention. This invention intends to extract a sample, and leave behind a container and needle which can safely be disposed of without risking exposure of the technician to it.

For this purpose, needle 20 (sometimes referred to as a piercer and extractor) has a sharp point 22 on its first end 23 of its smooth body 24, which body extends along central axis 25.

This body has a first channel 26 and a second channel 27. Both channels are closed at the first end 23, and are open at their respective second ends 28,29. The term channel is used in the sense of a tubular conduit. The body carries a collar 30 which can be grasped manually or by a mechanism to move the needle axially.

First channel 26 has a side port 31. Second channel 27 has a side port 32. Importantly, side port 31 is farther from the free end than side port 32. This enables port 32 to be submerged while port 31 still remains above the surface 33 of the specimen.

First channel 26 is connectible to a pressure source 34 which supplies air under pressure. The pressure source may be a pump, a bulb, or even a puff of air blown by the technician.

Second channel 27 is to deliver the sample to its container 21. When air pressure is delivered through channel 26, fluid is displaced through channel 27. The needle is moved to follow the downward movement of the surface to keep port 32 submerged. This movement of the needle can be accomplished manually or with mechanisms, both being done with reference to the location of the surface and of the interface between the blood fractions.

The utility of this invention is not limited to blood specimens or to risking specimens. It is useful in the extraction of any fluid from any closed container. The needle is sufficiently affordable as to be a discardable item which can be disposed of in systems conventionally provided for the disposal of potentially contaminated material.

This invention is not to be limited by the embodiments shown in the drawings and described in the description, which are given by way of example and not of limitation, but only in accordance with the scope of the appended claims.

I claim:

1. A septum piercer and sample extractor for removing a sample from a specimen contained in a container closed by a penetrable septum, said piercer and extractor comprising:

a needle having a body with a central axis, an outer wall, a first end, a second end, and a sharp closed point on its first end, said needle extending axially and containing a first channel and a second channel, said channels extending toward said second end of said needle;

a first side port through said body into said first channel, and a second port through said outer wall into said second channel, said first side port being axially farther from said free end than said second side port, said channels being open near said second end of said needle; and means carried by said needle enabling said needle to be moved axially to pierce said septum and its first end to be moved into said container so one of said ports is submerged in a fluid sample in the container while the other of said ports remains out of said sample; whereby when said one of said ports is submerged in a sample, gas may be forced through the channel leading to the other of said ports to force fluid from the sample through said first named port and channel.

2. A septum piercer and sample extractor according to claim 1 in which said means comprises a collar fixed to said body.

3. A septum piercer and sample extractor according to claim 1 in which one of said channels at said other end is engageable with air pressure supply means, and the other of said channels is adapted to deliver extracted sample to an intended location.

4. A septum piercer and sample extractor according to claim 3 in which said enabling means comprises a collar fixed to said body.

* * * * *